United States Patent [19]

Messina

[11] 4,027,007

[45] May 31, 1977

[54] ANTIPERSPIRANTS FORMULATED WITH BORAX

[75] Inventor: Ralph P. Messina, Somerset, N.J.

[73] Assignee: Colgate-Palmolive Company, New York, N.Y.

[22] Filed: Mar. 13, 1973

[21] Appl. No.: 340,901

Related U.S. Application Data

[63] Continuation of Ser. No. 96,639, Dec. 9, 1970, abandoned.

[52] U.S. Cl. .................................. 424/46; 424/47
[51] Int. Cl.$^2$ ..................... A61K 9/14; A61K 7/38
[58] Field of Search .............................. 424/47, 46

[56] References Cited

UNITED STATES PATENTS

| | | | |
|---|---|---|---|
| 1,371,822 | 3/1921 | Tate | 424/68 |
| 2,114,599 | 4/1938 | Jones | 424/65 |
| 2,210,014 | 8/1940 | Teller | 424/65 X |
| 2,236,387 | 3/1941 | Wallace, Jr. et al. | 424/65 X |
| 2,294,140 | 8/1942 | Taylor | 424/68 |
| 2,765,213 | 10/1956 | Beekman | 424/154 X |
| 2,876,163 | 3/1959 | Garizio et al. | 424/68 |
| 3,014,844 | 12/1961 | Thiel et al. | 424/46 |
| 3,081,223 | 3/1963 | Gunning et al. | 424/46 |
| 3,325,367 | 6/1967 | Miechowski | 424/148 X |
| 3,555,146 | 1/1971 | Jones et al. | 424/47 |

FOREIGN PATENTS OR APPLICATIONS 987,301   3/1965   United Kingdom ................ 424/47

*Primary Examiner*—Dale R. Ore
*Attorney, Agent, or Firm*—Herbert S. Sylvester; Murray M. Grill; Norman Blumenkopf

[57] ABSTRACT

A non-staining aerosol antiperspirant comprising a suspension of an aluminum antiperspirant powder in an anhydrous system containing as the stain preventative, an effective amount of an electrolyte selected from the class consisting of alkali metal borates, polyphosphates, metaphosphates, citrates, silicates and tri-sodium nitrilotriacetate.

1 Claim, No Drawings

ANTIPERSPIRANTS FORMULATED WITH BORAX

This is a continuation of application Ser. No. 96,639 filed Dec. 9, 1970, now abandoned.

This invention relates to non-staining aerosol antiperspirant formulations.

Antiperspirant formulations have heretofore been made in the form of creams, lotions, powders, sticks, pads, sprays and the like. In recent years, the aerosol system has been developed wherein an aerosol composition is pressurized by a liquified gaseous propellant and packaged in a suitable container, such as a metal bomb. The most effective antiperspirant compounds utilized are the water soluble aluminum salts such as aluminum sulfate, aluminum chloride, aluminum chlorhydrate and the like in aqueous solution. However, water-containing aerosol antiperspirant formulations have been the cause of numerous problems inclusive of the corrosive action of the soluble aluminum salt, clogging of the valve of the container, dripping of the spray caused by too wet a spray, staining of clothes in contact with the spray, etc.

Consequently, applicant has eliminated the aforesaid problems by formulating a substantially anhydrous suspension of the antiperspirant powder in an organic propellant containing a minor but effective amount of a softening agent as the stain preventative.

Accordingly, it is a primary object of this invention to provide a non-staining antiperspirant composition.

Another object of this invention is to provide a non-corrosive, anhydrous aerosol antiperspirant.

Still another object is the provision of a stabilized aluminum antiperspirant powder in an aerosol composition.

It has now been found that a non-staining antiperspirant aerosol composition can be provided comprising a substantially anhydrous suspension of an aluminum compound powder in a liquified gaseous propellant containing a minor amount of a softening agent capable of functioning as a stain inhibitor.

It is essential that the aluminum compound be in powdered form in order to minimize or eliminate clogging of the valve of the aerosol container as well as to provide greater and more effective coverage of the antiperspirant spray. An aluminum compound which will pass a 200 mesh screen and has a maximum particle size of 74 microns is suitable, the preferred maximum particle size being 50 microns and capable of passing a 325 mesh screen. Any aluminum compound having astringent and antiperspirant properties and which is insoluble in the propellant can be utilized such as aluminum sulfate, aluminum chloride, aluminum chlorhydrate, ether complexes of aluminum chlorhydrate and mixtures thereof. The preferred aluminum compounds are the aluminum chlorhydroxide complex [$Al_2(OH)_5CL \cdot 2H_2O$] and the polyhydric alcohol ether complexes thereof including the complexes of ethylene glycol, propylene glycol, 1,4-butanediol, diethylene glycol, dipropylene glycol, triethylene glycol, tetraethylene glycol, 1,3-butanediol, etc. A particularly useful complex thereof is the reaction product of aluminum chlorhydroxide with propylene glycol sold by the Reheis Chemical Company as "Rehydrol ASC" which is a white, free-flowing powder having an average particle size of 50 microns. The amount of active aluminum compound found suitable in the instant antiperspirant formulations is about 0.5% to 10% and preferably 2% to 5% by weight of the total composition.

It is preferred to add a non-volatile, non-hygroscopic organic ester to the aerosol composition to assist in dispersing the powdered aluminum antiperspirant in the propellant, provide lubricity to the particles, provide a wet spray whereby the adhesion of the powder to the skin is increased and to generally enhance the antiperspirant properties of the formulation. Esters utilizable herein may be the reaction product of a higher fatty acid or of an aromatic acid with an aliphatic alcohol containing from 1 to 3 hydroxy radicals. Specific examples of suitable esters include isopropyl myristate, butyl stearate, glyceryl trioleate, propylene glycol monooleate, stearyl palmitate, isopropyl myristate-palmitate, dimethylphthalate, and similar organic esters. The amount of organic ester utilized in instant invention is generally about 0.5–12% and preferably about 5–8% of the total composition.

Another preferred additive to the instant formulation is a suspending agent which retards agglomeration of the particles, decreases the settling rate of the particles and increases the viscosity of the aerosol suspension such as colloidal silica. The suspending agent functions to slow down the resettling of the aluminum compound after the container is shaken just prior to use. In addition, these agents also reduce the compacting of the aluminum compounds which would take place if they weren't used. The reduction in compacting effects an improvement in the redispersibility of the aluminum salts. A product found particularly useful herein is "Cab-O-Sil", a colloidal silica available from Godfrey L. Cabot, Boston, Massachusetts, which has a particle size below about 5 microns. Cab-O-Sil M-5 specifically utilized herein, is a submicroscopic particulate silica prepared in a hot gas environment of about 1100° C by the vapor phase hydrolysis of a silicon compound. Colloidal clays can also be utilized herein. In general, colloidal silica in amounts up to about 1% by weight of the total composition and preferably about 0.05 to 0.5% has been found useful in instant composition.

Although not essential for this invention, it is preferred to add a non-irritating, non-toxic germicide or bactericide in amounts of about 0.02 to 0.5% by weight of the total composition. Suitable antiseptic agents include dichlorophene, hexachlorophene, and any bacteriostats commonly known in the market.

Perfume is desirable, but not essential additive in amounts within the range of about 0.05 to 1% by weight of the total composition. It is apparent that the addition of perfumes renders the product more saleable. Satisfactory perfumes include oil or lavender, oil of sandalwood, geranium, commercial perfumes presently on the market and mixtures thereof.

Minor amounts of other ingredients may be added which are non-irritating to the skin and do not adversely interfere with the functions of instant composition, inclusive of non-ionic, cationic, anionic and amphoteric surfactants, anhydrous lower and higher aliphatic alcohols, etc.

Any conventional liquified, gaseous propellant or mixture of propellants may be used that has the desired vapor pressure at atmospheric temperature to effectively dispense the aerosol composition from the spray container. Suitable propellants include low molecular weight aliphatic hydrocarbons and halogenated hydrocarbons containing from 1 to 4 carbon atoms, and mixtures thereof. Examples of aerosol propellants used either alone or in admixture are propane, isobutane, trichlorofluoromethane ("Freon 11"), dichlorofluoromethane ("Freon 12"), tetrafluorodichlorethane ("Freon 114"), trichlorotrifluoroethane ("Freon 113"), pentafluoromonochloroethane ("Freon 115"), cyclic hexafluorodichlorobutane ("Freon C 316"), octafluoropropane ("Freon 218"), cyclic octafluorobutane ("Freon C 318"), propane, butane, pentane, isobutane, etc. By suitably selecting the combination of liquified propellants, the spray can be adjusted to be soft and dry or heavier and wetter. The particular combination of propellants is also determinative of the range of the spray, namely short full bursts or a long fine spray. The propellant is non-reactive with the aerosol ingredients, functioning only as a vehicle therefor. The amount of propellant may constitute as much as 95% and as little as 60% by weight of the total composition, with about 85 to 95% being preferred.

An essential ingredient of instant composition is a stain inhibitor comprising an inorganic and organic electrolyte of the type which functions as a water softening agent when added to a washing medium. Generally, the alkali metal polyphosphates, metaphosphates, borates, citrates, silicates and tri-sodium nitrilotri-acetate have been found to be most effective as stain inhibitors. Although the sodium and potassium salts are preferred, their equivalents such as cesium, rubidium and lithium salts can also be used. It is also desirable that the electrolyte be in a finely divided condition, preferably of a particle size sufficiently small to pass through a 325 mesh screen. Specific examples of stain inhibitors include $Na_5P_3O_{10}$, $Na_4P_2O_7$, $Na_2H_2P_2O_7$, potassium polyphosphates, potassium silicate, sodium silicate, borax, sodium citrate, potassium citrate, etc. The amount of electrolyte must be sufficient to provide a non-staining aerosol composition, generally in amounts of about 1-5% and preferably 0.5 to 3% by weight of the total composition. The stain inhibitors of this invention are normally present during laundering of fabrics at which time these agents aid in the washing off of stains by acting as a sequestering agent of heavy metal ions, by buffering the wash solution to retain its alkalinity, and by retaining the soil particles in suspension during the washing operation. It is therefore unexpected and dramatic that these compounds will provide a high degree of protection against staining by virtue of being deposited onto the fabric adjacent the body treated with instant antiperspirant aerosol spray.

It is essential to the invention that the formulation be substantially anhydrous. Moisture renders the aluminum chlorhydroxide chemically active because of its solubility in water, thereby causing numerous problems such as corrosion of the metal container, agglomeration of the aluminum compound within the container, clogging of the valve, hydrolysis of the antiperspirant within container, reducing its effectiveness. The absence of water eliminates aforesaid difficulties since the aluminum compound remains chemically inert and suspended in the propellant until after it is sprayed and reaches the skin of the user, at which time the moisture on the body activates the aluminum compound by dissolution.

The compositions of this invention are readily prepared by any of the methods commonly used in the art of preparing self-propelling aerosol formulations. The aluminum compound powder is thoroughly mixed with the other ingredients such as suspending agent (colloidal silica), dispersing and lubricating agent (organic ester), electrolytic stain inhibitor, bacteriostat, perfume, etc. to form a stable, homogeneous dispersion, which is normally in the form of a concentrate. A liquified gaseous propellant, is added to said concentrate within the confines of a container, whereby a self-propelling pressurized aerosol composition is produced. The aluminum compound powder remains uniformly suspended in the organic propellant and retains its stability for a protracted period of time. The powder is discharged from the container with ease and adheres to the skin in the form of a fine, dry spray.

The following examples are designed to merely illustrate but not limit the scope of this invention. Unless otherwise indicated, all parts and percentages are based on weight.

EXAMPLE I

| % by weight | Components |
| --- | --- |
| 3.0 | Aluminum chlorhydroxide complex powder |
| 0.35 | Cab-O-Sil M5 |
| 6.50 | Isopropyl myristate |
| 1.00 | Borax (passed through a 325 mesh screen) |
| 0.10 | Hexachlorophene |
| 0.20 | Perfume |
| 88.85 | *Propellant 11/12 60:40 |

*Propellant 11-Trichloromonofluoromethane
Propellant 12-Dichlorofluoromethane

The hexachlorophene is mixed with isopropyl myristate until dissolved therein. Proportionate amounts of the aluminum chlorhydroxide powder and "Cab-O-Sil" are slowly added to the ispropyl myristate with continuous mixing. Borax is added to the above mixture, followed by the perfume while continuing the mixing.

After all the ingredients are thoroughly mixed, the homogeneous dispersion is passed through an homogenizer at a setting of about 1000-1200 psig.

11.15% of the above concentrate is placed in an aerosol can, a valve crimped on, and the can is pressurized with 88.5% of the propellant.

Fabric adjacent the axilla treated with the aerosol spray of Example 1, exhibited substantially no yellowing or other staining before or after laundering.

EXAMPLE 2

The same procedure is followed as in Example 1, except that the homogenizing step is omitted.

EXAMPLE 3

The same procedure is followed as in Example 2, except that 3% sodium citrate is substituted for the 1% borax and the propellant is reduced to 86.85%.

The resultant products are all non-staining, stable, homogeneous dispersions of aluminum chlorhydroxide powder in propellant which are non-corrosive to the aerosol cans. The powdered spray delivered from the container is fine and dry and adheres to the skin as an effective antiperspirant.

It will be apparent that many changes and modifications of the several features described herein may be made without departing from the spirit and scope of the invention. It is therefor apparent that the foregoing description is by way of illustration of the invention rather than limitation thereof.

What is claimed:
1. A method for reducing the staining potential of a powder aerosol antiperspirant composition admixing as a stain inhibitor about 0.1 to 5% of finely divided borax, having a particle size such that it passes through a 325 mesh screen, with a substantially anhydrous suspension, in about 85 to 95% of a liquified, gaseous propellant, of about 0.5 to 10% of finely divided astringent antiperspirant aluminum chlorhydroxy powder having a particle size such that it passes through a 200 mesh screen.

* * * * *